Figure 1:
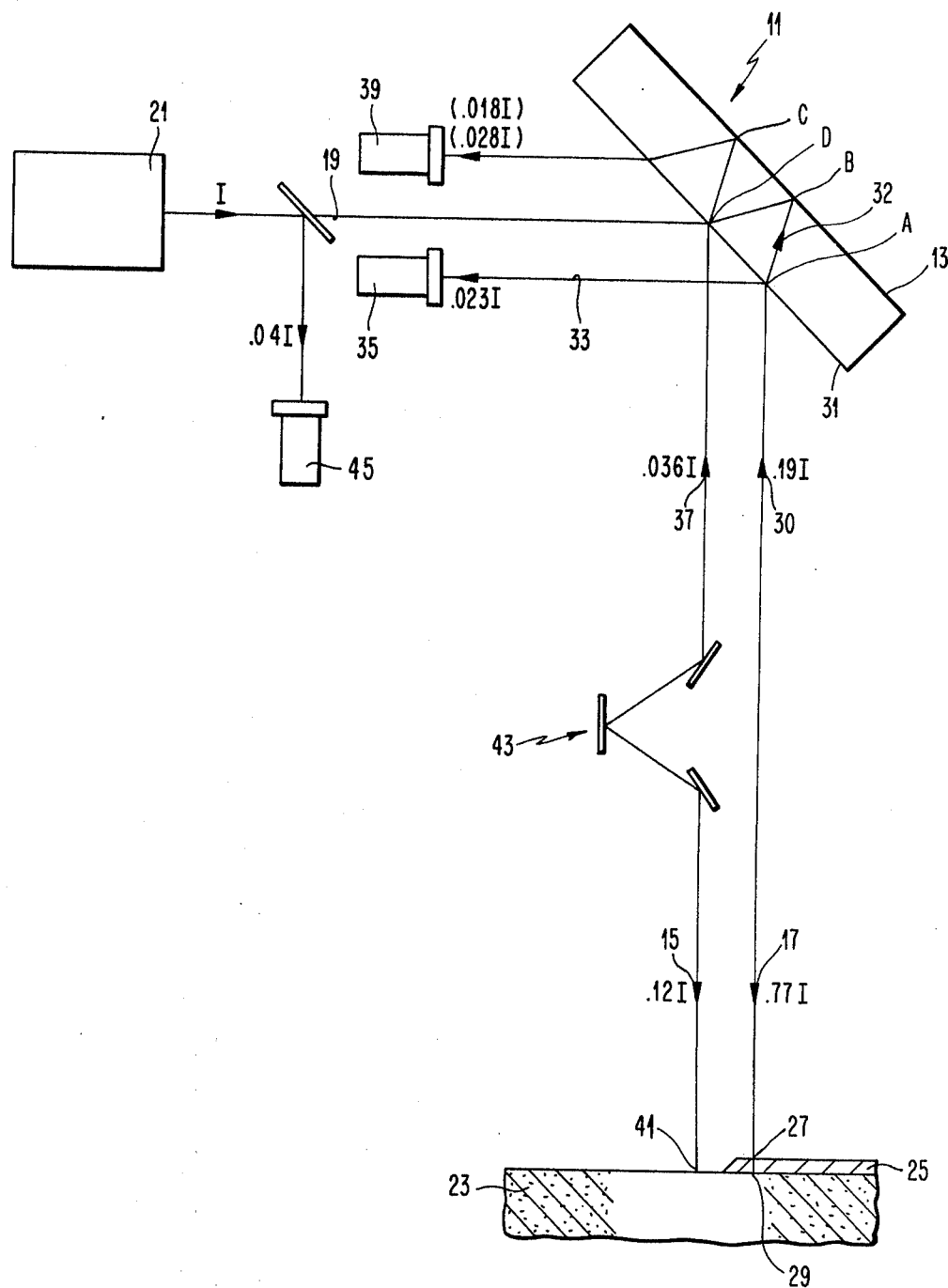

United States Patent [19]

Habegger

[11] 4,147,435
[45] Apr. 3, 1979

[54] INTERFEROMETRIC PROCESS AND APPARATUS FOR THE MEASUREMENT OF THE ETCH RATE OF OPAQUE SURFACES

[75] Inventor: Millard A. Habegger, Boulder, Colo.

[73] Assignee: International Business Machines Corporation, Armonk, N.Y.

[21] Appl. No.: 811,741

[22] Filed: Jun. 30, 1977

[51] Int. Cl.² .................................................. G01B 9/02
[52] U.S. Cl. ..................................................... 356/357
[58] Field of Search ................... 356/106 R, 108, 109, 356/113

[56] References Cited

U.S. PATENT DOCUMENTS 3,612,692  10/1971  Kruppa ................................. 356/108
3,930,730  1/1976  Laurens et al. ...................... 356/109

Primary Examiner—Conrad J. Clark
Attorney, Agent, or Firm—David M. Bunnell

[57] ABSTRACT

An interferometer system and process for detecting etch rates in opaque materials, such as silicon or metal, has means for producing a pair of parallel light beams, one of which is directed to the surface of the opaque material and the other of which is directed to the surface of an adjacent transparent masking material. The rate of etch of the opaque material is determined by detecting and recording the changes of light intensity due to interference between the beam reflected from the opaque layer and the beam reflected from the opaque layer beneath the transparent masking material.

5 Claims, 4 Drawing Figures

INTERFEROMETRIC PROCESS AND APPARATUS FOR THE MEASUREMENT OF THE ETCH RATE OF OPAQUE SURFACES

BACKGROUND OF THE INVENTION

Detection apparatus for monitoring the rate of change of thickness of a transparent layer using light interference techniques is known. For example, in etching a layer of silicon dioxide on a silicon substrate through a resist window using a reactive gas plasma, a monochromatic light beam is directed onto the surface of the oxide. The light beam, which is conveniently produced by a laser source, is reflected from both the surface of the oxide and from the surface of the underlying opaque silicon. These reflections interfere with one another which varies the light intensity as the thickness of the oxide layer changes. The light intensity changes are sensed by a detector and recorded in the form of a trace. When the trace goes through one period of oscillation, the thickness of the $SiO_2$ layer has changed by $\lambda/2n$ where $\lambda$ is the wavelength of the light and n is the refractive index of the $SiO_2$. This system is essentially a two beam interferometer in which the two beams are parallel to a high degree of accuracy. The small angle between the two beams results in the interference fringe width being practically the width of the laser beam on the detector. This system is, however, not useful in determining the rate of change of thickness of opaque materials such as silicon or metal.

An interferometric system and process has now been devised which can determine the rate of etch of opaque materials.

BRIEF SUMMARY OF THE INVENTION

In accordance with the invention, an interferometer system and process are provided for detecting the rate of etch of an opaque layer which is partially masked by a transparent layer which is also etched. Two parallel beams of monochromatic light are formed with the first beam being incident on the opaque layer to be etched and the second beam being incident on the transparent layer. The rate of etch of the transparent layer is determined by detecting and recording changes in light intensity due to the interference between the reflections of the second beam from the top of the transparent layer and from the surface of the opaque layer beneath the transparent layer. One period of oscillation of the light intensity corresponds to a thickness change in the transparent layer of $\lambda/2n$ where $\lambda$ is the wavelength of the light and n is the refractive index of the transparent layer. The rate of etch of the opaque layer is determined by detecting and recording the changes in light intensity due to the interference between the first beam reflected from the opaque layer and the second beam reflected from the opaque layer beneath the transparent layer. In this case, one period of oscillation of the light intensity corresponds to the removal of an opaque layer thickness of $\lambda/2 - \Delta X(n-1)$, where $\lambda$ is the wavelength of the light, n is the refractive index of the transparent layer and $\Delta X$ is the transparent layer thickness removed during the same period as determined above.

Turning now to FIG. 1, parallel precision window 11 with an aluminized back surface 13 is mounted at an angle of 45° and produces two separate parallel beams 15 and 17 from single beam 19 coming from HeNe laser light source 21. Window 11 is a mirror whose plane surfaces are parallel to an accuracy of a few seconds of arc. The thickness of window 11 can vary and is chosen to give a sufficient beam separation so that beam 15 can be directed onto the opaque layer 23 and beam 17 can be directed onto the transparent layer 25. A thickness of about ¼" is used to accomplish this in the described embodiment. The mounting angle of window 11 can be varied so long as the light source and the window are arranged to make the beams 15 and 17 normal to the surfaces of the materials being etched. In this way, the returning beams 30 and 37 are colinear with the incident beams 15 and 17. Although it is convenient to use a laser source, other sources of monochromatic light could be used such as a tungsten or mercury lamp with a narrow bandpass filter.

Beam 17 is reflected from both the surface 27 of transparent layer 25 and the underlying surface 29 of opaque layer 23 to form returning beam 30 which consists of the interfering reflected beams from surfaces 27 and 29. Beam 30 passes back along the path of beam 17 to the front surface 31 of window 11 at point A. The combined reflected interfering beams 33 from point A of front surface 31 are directed to a detector 35 which can be, for example, a photomultiplier, solar cell or diode.

Portion 32 of the returning beam 30 from surfaces 27 and 29 passes through front surface 31 and is reflected twice off of back surface 13, at points B and C, and once partially off of front surface 31 at point D. It is then directed to a detector 39 which can be the same type as detector 35. The returning beam 37 from beam 15 which is incident on uncovered or free surface 41 of opaque layer 23 passes through front surface 31 of window 11 at point D and is reflected once off of the back surface 13 of window 11 at point C and is then directed to detector 39. Beam 37 is colinear with and interferes with portion 32 of beam 30 beginning at point D.

A pathlength compensator 43 is used to equalize the paths of the two highest intensity beams falling on detector 39 which are the returning beam 37 from the uncovered opaque layer surface 41 and the reflected beam from the underlying opaque layer surface 29. Without compensator 43, pathlength differences between the beams would produce a noisy signal on detector 39 due to the fact that laser 21 may be switching modes within the short time period equal to the path difference divided by the velocity of light. Practically, pathlength differences need only be equalized to an accuracy of a few millimeters.

The pathlength compensator need not be built with tight angle tolerances in order to maintain the parallelism of the two beams. The only requirement is that the optical elements have flat surfaces so that the returning beam sees precisely the same angles as the down going beam.

In order to obtain the desired output signal from detector 39, the intensity ratios of the beams are adjusted as shown in FIG. 1 where I is the intensity of the light from laser 21. The values 0.018 I and 0.028 I impinging on detector 39 are the reflections from surfaces 29 and 41 respectively. This is done by either selecting the refraction index of the window 11 to be about 1.5 or by adjusting the transmittance of backsurface 13. The polarization of beam 19 should be perpendicular to the plane of FIG. 1. Glass window 11 should have its two faces parallel to an accuracy of a few seconds of arc in order to avoid the introduction of an angle greater than a milliradian between the two highest intensity beams on detector 39. The larger the angle between the two beams, the narrower will be the interference fringe spacing due to the angle between the two beams on detector 39. This fringe spacing should be maintained as wide as possible to minimize any problems associated with vibrations or low level signals. Detector 45 samples beam 19 and the output of detector 45 is used as a reference for detectors 35 and 39 as shown in the detection circuit in FIG. 2.

The substrate to be etched, for example a silicon wafer which is partially covered with a patterned layer of transparent resist material is placed under beams 15 and 17, with beam 15 incident on the base silicon and beam 17 incident on the resist. Window 11 is adjusted so that the returning reflected beams are centered on the detectors. Because the beams 15 and 17 are relatively close to each other, they both pass through essentially the same media so that the introduction of windows, vacuum and/or variations in the atmosphere have a minimal effect on the detector output.

Figure 2:
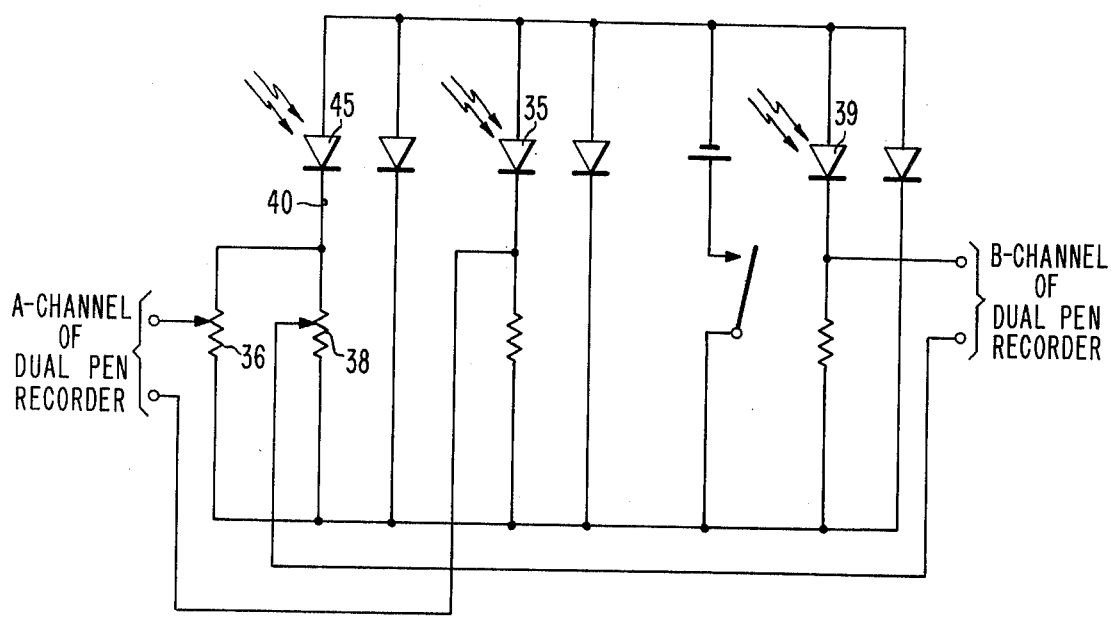
Figure 3A:
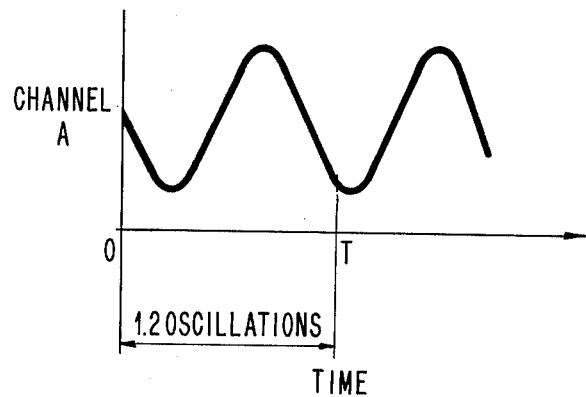
Figure 3B:
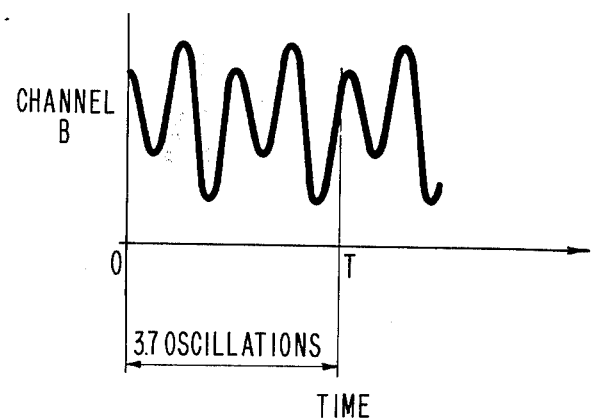

The etching process is started using, for example, a reactive gas plasma and the output from detectors 35 and 39 drive the A and B channels of a dual pen recorder as shown in FIG. 2. Before an etch is started, the potentiometers 36 and 38 on the output 40 are adjusted so that a null output is obtained from detectors 35 and 39. In this manner, light source amplitude variations on the recorder traces are greatly minimized. Typical recorder traces are illustrated in FIGS. 3A and 3B. The A channel trace obtained from detector 35 represents the periodic change in light intensity caused by the changing interference between the reflected beams from surfaces 27 and 29 as the thickness of layer 25 changes due to the etching process. When the A channel trace goes through one period of oscillation, the thickness of layer 25 has changed by $\lambda/2n$, where $\lambda$ is the wavelength of the light and n is the refractive index of the resist layer. The highest amplitude oscillations of the B channel trace represent the periodic change in light intensity caused by the changing interference between the beams reflected from uncovered surface 41 and underlying surface 29 as the etching process proceeds. These oscillations are amplitude modulated as a result of the resist being etched. One cycle of the B channel trace corresponds to the removal of a silicon thickness of $\lambda/2-\Delta X(n-1)$, where $\lambda$ is the wavelength of light, n is the refractive index of the resist and $\Delta X$ is the thickness of resist removed in the same time as deduced from the A channel recorder trace. In this manner the etch rate of the resist and silicon are simultaneously determined by the system. In the example illustrated in FIGS. 3a and 3b, in a time, T, the channel A trace has gone through 1.2 oscillations so that the amount of resist thickness removed, $\Delta X$, equals $1.2\lambda/2n$. In the same time period the B channel trace has gone through 3.7 oscillations so that the amount of opaque material thickness removed during time, T, is given by $3.7\lambda/2-1.2\lambda(n-1)/2n$. The etching process can be stopped when any desired thickness of the opaque layer has been removed as determined above.

Although the invention has been particularly shown and described with reference to preferred embodiments thereof, it will be understood by those skilled in the art that the foregoing and other changes in form and detail may be made therein without departing from the spirit and scope of the invention.

What is claimed is:

1. An interferometer system for determining the etch rates of an opaque material and an overlying transparent layer which partially masks the opaque material comprising:

a light source having a wavelength $\lambda$, means for dividing the light into two parallel beams one of which is directed onto the free surface of the opaque material and the other of which is directed onto the transparent layer in a direction perpendicular to the surfaces of the layers, a first detector means located in the path of the interfering reflected beams returning from the surface of the transparent layer and from the underlying surface of the opaque material to measure and record the change in light intensity of the interfering reflected beams as a function of time with one period of oscillation of the light intensity corresponding to a thickness change in the transparent layer of $\lambda/2n$ where n is the refractive index of the transparent layer, a second detector means located in the path of the interfering reflected beams returning from the free surface of the opaque material and from the underlying surface of the opaque material to measure and record the change in light intensity of the interfering reflected beams as a function of time with one period of oscillation of the light intensity corresponding to the removal of an opaque layer thickness of $\lambda/2-\Delta X(n-1)$, where $\Delta X$ is the thickness change of the transparent layer during the same period of time.

2. The system of claim 1 wherein the means for dividing the light into two parallel beams is a window having a back reflective surface.

3. The system of claim 1 including means to equalize the pathlength of said parallel beams.

4. The system of claim 1 wherein said light source is a laser.

5. A process for determining the etch rates of an opaque material and an overlying transparent layer which partially masks the opaque material comprising:

providing a light source having a wavelength $\lambda$, dividing the light into two parallel beams one of which is directed onto the free surface of the opaque material and the other of which is directed onto the transparent layer in a direction perpendicular to the surfaces of the layers, detecting the light from the interfering reflected beams returning from the surface of the transparent layer and from the underlying surface of the opaque material and measuring and recording the change in light intensity of the interfering reflected beams as a function of time with one period of oscillation of the light intensity corresponding to a thickness change in the transparent layer of $\lambda/2n$ where n is the refractive index of the transparent layer, detecting the light from the interfering reflected beams returning from the free surface of the opaque material and from the underlying surface of the opaque material and measuring and recording the change in light intensity of the interfering reflected beams as a function of time with one period of oscillation of the light intensity corresponding to the removal of an opaque layer thickness of $\lambda/2-\Delta X(n-1)$, where $\Delta X$ is the thickness change of the transparent layer during the same period of time.

* * * * *